United States Patent [19]

Graceffa et al.

[11] Patent Number: 5,154,903
[45] Date of Patent: Oct. 13, 1992

[54] TREATMENT OF ASBESTOS AND SILICATES TO REDUCE THEIR TOXICITY

[75] Inventors: Philip J. Graceffa, Newtonville, Mass.; Sigmund A. Weitzman, Winnetka, Ill.

[73] Assignees: Massachusetts General Hospital; Boston Biomedical Research Institute, both of Boston, Mass.

[21] Appl. No.: 581,773

[22] Filed: Sep. 13, 1990

[51] Int. Cl.$^5$ .................... A61K 31/66; A61K 31/195; C01B 33/20; C01B 33/24
[52] U.S. Cl. .................................... 423/326; 423/331; 514/121; 514/566
[58] Field of Search ................ 514/121, 566; 423/326, 423/331

[56] References Cited

U.S. PATENT DOCUMENTS 4,474,742 10/1984 Graceffa et al. .................... 423/331

OTHER PUBLICATIONS

Rasmussen, L. et al., In Vitro Cell Dev Biol 22(4):177–179 (Apr. 1986).
Vullo, C. et al., Haematologica 74 (5 Suppl): 241–25) (Oct. 1989).
Waxman, H. S. et al., Prog Hematol 6:338–373 (1969).
Winston, G. W. et al., Arch Biochem Biophys 232(1):378–390 (Jul. 1984).
Henriksson, R. et al., Cancer Lett. 43(3):179–183 (Dec. 15, 1988).
Morehouse, L. A. et al., Arch Biochem Biophys 232(1):366–377 (Jul. 1984).
Pippard, M. J. et al., Scand J Haematol 36(5):466–472 (May 1986).
Pitt, C. G. et al., "Development of Iron Chelators for Clinical Use" Nih, Bethesda (1976).
Timbrell, V., "Characteristics of the International Union Against Cancer Standard Reference Samples of Asbestos", pp. 2–10 (1969).
De Waele, J. K. and F. C. Adams, Scanning Microscopy 2:209–228 (1988).
Harrington, J. S., Annals New York Academy of Sciences, 132:31–47 (1965).
Pooley, F. D., Seminars in Oncology, 8:243–249 (1981).
Weitzman, S. A. and P. Graceffa, Arch. Biochem. Biophys. 228:373–376 (1984).
Graf, E. et al., J. Biol. Chem. 259:3620–3624 (1984).
Zalma, R. et al., Can. J. Chem. 65:2338–2341 (1988).
Kennedy, T. P. et al., Arch. Biochem. Biophys. 269:359–364 (1989).
Graf, E., JAOCS 60:1861–1867 (1983).
Graf, E. and J. W. Eaton, Cancer 56:717–718 (1985).
Gulumian, M. and J. A. Van Wyk Chem. Biol. Interactions 62:89–97 (1987).

Primary Examiner—Frederick E. Waddell
Assistant Examiner—Diane Gardner
Attorney, Agent, or Firm—Hamilton, Brook, Smith & Reynolds

[57] ABSTRACT

This invention pertains to an improved method of inhibiting peroxide-reduction catalytic activity and concomitant toxicity of asbestos and nonasbestos iron-containing silicates. These undesirable reactions can be substantially reduced or essentially eliminated by contacting these potentially harmful materials with an aqueous solution comprising a non-mutagenic non-toxic iron chelating agent, such as phytic acid, diethylenetriamine pentaacetic acid (DTPA) or derivatives of these.

7 Claims, No Drawings

TREATMENT OF ASBESTOS AND SILICATES TO REDUCE THEIR TOXICITY

BACKGROUND OF INVENTION

The various forms of asbestos, among which are chrysotile, crocidolite and amosite, have been found to be toxic toward mammals, particularly when inhaled. They typically produce inflammation, fibrous scarring and cancer. While it appears that the size of asbestos fibers are important in determining the amount of toxicity produced, the nature of the chemical interaction between asbestos and cells is also important.

One feature of the response to inhalation of asbestos fibers is the fiber attachment to and/or engulfment by phagocytic cells (the pulmonary macrophages) and subsequent inflammation. The inflammatory phagocytes reduce oxygen to reactive metabolites, such as the superoxide anion radical, hydrogen peroxide and the hydroxyl radical. The hydroxyl radical is a potent oxidizing agent which initiates lipid peroxidation, kills bacteria, damages cellular DNA, and reacts with most organic molecules. This radical is ordinarily generated by stimulated phagocytes in concentrations much lower that those of the other, more stable, reduced oxygen species: superoxide and hydrogen peroxide. While these latter species may be produced by direct enzymatic reduction of oxygen, it is believed that under physiological conditions, generation of hydroxyl radicals is a secondary process catalyzed by metals, such as iron or copper.

It has been proposed to treat asbestos with various metal salts, including iron salts, to reduce its biologically harmful properties by way of metal-micelle formation. U.S. Pat. No. 4,328,197. The chelating agent disodium ethylenediamine tetraacetic acid (EDTA) has also been reacted with asbestos and shown to be less harmful to living cells. U.S. Pat. Nos. 4,168,346, 4,234,377 and 4,309,477. However, EDTA has been shown to enhance rather than inhibit the peroxide catalytic activity of asbestos. Weitzman, S. A. and P. Graceffa, *Arch. Biochem. Biophys.* 220:373-376 (1984).

Asbestos contains iron as part of its crystalline structure and/or as a contaminant. The presence of iron in asbestos has been shown to catalyze hydroxyl and superoxide radical generation from hydrogen peroxide which is a normal by-product of tissue metabolism. Weitzman, S. A. and P. Graceffa, *Arch. Biochem. Biophys.* 228:373-376 (1984). They found that a hydroxamic acid iron chelating agent, desferroxamine, could complex the asbestos iron and inhibit its ability to produce hydroxyl radicals. Toxicity of asbestos can be inhibited or reduced by treating asbestos with other non-mutagenic non-toxic hydroxamic acid iron chelating agents, such as desferrichromes, fusarinines, myobactin P., mycchanamide, hadacidin, aspergillic acid, pulcherriminic acid, rhodotarulic acids, and citrate-hydroxaminic acids, and salts thereof. Graceffa, P. and S. A. Weitzman, U.S. Pat. No. 4,474,742, issued Oct. 2, 1984.

Nonfibrous silicates have also been shown to produce toxic hydroxyl radicals in the lung by a mechanism similar to asbestos. Kennedy T. P. et al., *Arch. Biochem. Biophys.*, 269:359-364 (1989); Gulumian M. and J. A. Van Wyk, *Chem.-Biol. Interactions* 62:89-97 (1987).

Although hydroxyl radical production can be inhibited by such treatment, the cost of desferroxamine is prohibitively high for the large amount of asbestos that requires treatment. Thus, it would be desirable to provide a method for inhibiting peroxide-reduction catalytic activity of asbestos using an iron complexing agent which is abundant, relatively inexpensive and nontoxic.

SUMMARY OF THE INVENTION

This invention pertains to an improved method of inhibiting the peroxide-reduction catalytic activity and concomitant toxicity of asbestos and nonasbestos iron-containing silicates. These undesirable reactions can be substantially reduced or essentially eliminated by contacting asbestos or nonasbestos silicates with an aqueous solution comprising a non-mutagenic non-toxic iron chelating agent, such as phytic acid, diethylenetriamine pentaacetic acid (DTPA) or derivatives of these. The method can be used to substantially reduce or eliminate the toxicity and carcinogenicity of these potentially toxic materials.

DETAILED DESCRIPTION OF THE INVENTION

It has been previously shown that hydrogen peroxide produces highly toxic hydroxyl radicals in the presence of iron. Based on this phenomenon, the present invention provides an improved method of inhibiting the peroxide-reduction catalytic activity of asbestos (e.g., chrysotile, amosite and crocidolite) or nonasbestos iron-containing silicates (e.g., glass fibers) by treating them with phytic acid, DTPA or derivatives of these. For example, the chelating agent can be a hydrated dodecasodium salt of phytic acid or an ester of phytic acid.

According to the invention, the chelating agent is contacted with untreated asbestos or nonasbestos silicates and forms a complex with iron present in these materials, i.e., the chelating agent binds $Fe^{+3}$ and/or $Fe^{+2}$. The amount of chelating agent applied to the asbestos or nonasbestos silicates should be sufficient to bind substantially all of the iron present therein. The chelated iron can then be blocked from catalyzing the reduction of hydrogen peroxide and/or oxygen into toxic hydroxy-radicals. By this method, iron can be blocked by chelation or actually removed from the asbestos or silicate by leaching the $Fe^{+2}$ and/or $Fe^{+3}$ therefrom. Thus, the catalytic activity of these potentially harmful materials can be substantially reduced or even eliminated.

The conditions under which the chelating agent is contacted with the iron-containing material (i.e., asbestos or silicate) is not critical for one to practice the invention. It can be applied to an asbestos or nonasbestos silicate-containing area by various means, such as by spraying or coating an aqueous solution of the chelating agent to the area. For example, when asbestos is present in particulate form, it can be treated by stirring or mixing it in the aqueous solution at room temperature. Preferably, the aqueous solution will contain from about 0.1 to about 100 mM of the iron-chelating agent. The minimum effective amount of iron-chelating agent varies depending upon the chelator used and type of asbestos or nonasbestos iron-containing silicate to be treated. In general, $10^{-6}$ parts by weight of the chelating agent is the minimum amount required for effective treatment of asbestos by weight. In one embodiment, asbestos particles can be first suspended in water, after which the chelating agent or concentrated aqueous solution thereof can be added.

Treatment with a chelating agent to block the coordination sites of iron can be widely used as part of the standard chemical washing treatment performed prior to asbestos removal from buildings or prior to working in areas where asbestos is present. Alternatively, asbestos can be treated during its manufacture or prior to use as insulation. Such treatment could effectively reduce and/or eliminate the risk of contracting asbestos-related diseases for those in contact with asbestos. Likewise, iron-containing silicates can be treated with the chelating agents of this invention to reduce the peroxide-reduction catalytic effect of these materials.

Phytic acid is a naturally occuring compound which is present in food products and is an abundant plant constituent and waste product in the food and milling industry. It is relatively inexpensive, and therefore, economically it is an excellent candidate for treating the large quantity of asbestos that presently exists in schools, homes and other buildings. Accordingly, phytic acid is substantially non-toxic and non-mutagenic to humans and, thus, may be used to treat persons exposed to asbestos.

Phytic acid, DTPA, physiologically acceptable salts thereof or combinations of these chelating agents can be administered to a patient in a physiologically acceptable vehicle and in an amount sufficient to inhibit the peroxide-reduction catalytic activity of asbestos or silicates inhaled by the person to be treated. An effective amount of iron chelating agent(s) can be ascertained by those of skill in the art based upon body size of the individual being treated and the degree of exposure and amount of the asbestos or iron-containing silicate inhaled. Reduction or elimination of hydroxyl radical generation may be critical to reducing the toxicity and carcinogenicity of these potentially toxic materials.

The invention will be further illustrated by the following Exemplification.

EXEMPLIFICATION

Generation of hydroxyl radicals in the presence of hydrogen peroxide was determined for treated and untreated asbestos. The hydroxyl radical was assayed by the electron spin resonance (ESR) technique of spin trapping using 5,5-dimethyl-1-pyrroline-N-oxide (DMPO) as the spin trapping agent.

Hydrogen peroxide was added to a final concentration of 0.3% to a solution containing 1-2 mg/ml crocidolite asbestos (U.I.C.C. Reference Standard Samples, 80-100 mM DMPO), in the absence or presence of iron chelators-diethylenetriamine pentaacetate (1 mM or 1 $\mu$M) or phytate (1 mM). A specimen of the resulting solution was then placed in a cuvette and inserted into a Varian E-109 x-band electron spin resonance spectrometer operating at 100 kHz field modulation, 2 gauss modulation amplitude and microwave power level 2 mW. ESR spectra were recorded three minutes after addition of hydrogen peroxide with a gain setting of $1.6 \times 10^4$ with a time constant of 0.064 seconds and scanned at a rate of 50 gauss/min.

In each case, the addition of hydrogen peroxide to the control caused the appearance of the characteristic spectrum of the hydroxyl radical adduct of the spin trapping agent, as described by Bannister et al. (*Biochem. Biophys. Acta* 715:116-120 (1982)). The level of hydroxyl radicals generated in the absence of the chelators was reduced to background levels in the presence of the chelators.

EQUIVALENTS

Those skilled in the art will recognize, or be able to ascertain, using no more than routine experimentation, many equivalents to the specific embodiments of the invention described herein. Such equivalents are intended to be encompassed by the following claims:

We claim:

1. A method of inhibiting the peroxide-reduction catalytic activity of iron-containing asbestos or an iron-containing silicate, comprising the step of contacting the asbestos or iron-containing silicates with an aqueous solution comprising an iron chelating agent selected from the group consisting of phytic acid and derivatives thereof, the amount of chelating agent being sufficient to bind substantially all iron present in the asbestos or silicate.

2. The method of claim 1, wherein the chelating agent is a hydrated dodecasodium salt of phytic acid.

3. The method of claim 2, wherein the step of contacting is carried out at room temperature.

4. The method of claim 1, wherein the asbestos is selected from the group consisting of chrysotile, amosite and crocidolite.

5. A method of inhibiting the peroxide-reduction catalytic activity of iron-containing asbestos, comprising the step of contacting the asbestos with an aqueous solution comprising a diethylenetriamine pentaacetic acid iron chelating agent or derivative thereof, the amount of chelating agent being sufficient to bind substantially all iron present in the asbestos.

6. The method of claim 5, wherein the step of contacting is carried out at room temperature.

7. The method of claim 5, wherein the asbestos is selected from the group consisting of chrysotile, amosite and crocidolite.

* * * * *